(12) United States Patent
Gagne et al.

(10) Patent No.: US 10,215,597 B2
(45) Date of Patent: *Feb. 26, 2019

(54) FLUID MONITORING ASSEMBLY WITH SENSOR FUNCTIONALITY

(71) Applicant: ALPHINITY, LLC, Carson City, NV (US)

(72) Inventors: Michael C. Gagne, Carson City, NV (US); Steven V. Cates, Lakewood, CA (US); Dean Richards, Simi Valley, CA (US); Scott Bendon, Wales (GB)

(73) Assignee: ALPHINITY, LLC, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/111,779

(22) PCT Filed: Jan. 16, 2015

(86) PCT No.: PCT/US2015/011791
§ 371 (c)(1),
(2) Date: Jul. 14, 2016

(87) PCT Pub. No.: WO2015/109209
PCT Pub. Date: Jul. 23, 2015

(65) Prior Publication Data
US 2016/0327416 A1    Nov. 10, 2016

Related U.S. Application Data

(60) Provisional application No. 61/928,905, filed on Jan. 17, 2014.

(51) Int. Cl.
*G01D 11/30* (2006.01)
*G01D 11/24* (2006.01)
(Continued)

(52) U.S. Cl.
CPC .......... *G01D 11/245* (2013.01); *G01D 11/30* (2013.01); *G01F 15/14* (2013.01); *G01L 19/144* (2013.01); *G01N 27/07* (2013.01); *G01D 18/008* (2013.01)

(58) Field of Classification Search
CPC .......... G01F 1/00; G01F 15/14; G01F 15/185; G01F 15/00; G01F 18/006; G01D 11/245; G01D 11/30; G01L 19/144; G01N 27/07
(Continued)

(56) References Cited

U.S. PATENT DOCUMENTS 3,563,095 A   2/1971 Robinson, Jr.
4,254,797 A   3/1981 Mayeaux
(Continued)

FOREIGN PATENT DOCUMENTS

CN    102183270 A A    9/2011
CN    102661423 A A    9/2012
(Continued)

OTHER PUBLICATIONS

PCT International Preliminary Report on Patentability (Chapter I of the Patent Cooperation Treaty) for PCT/US2015/011791, Applicant: Alphinity, LLC, Form PCT/IB/326 and 373, dated Jul. 28, 2016 (9 pages).
(Continued)

*Primary Examiner* — Harshad R Patel
*Assistant Examiner* — Nigel Plumb
(74) *Attorney, Agent, or Firm* — Vista IP Law Group LLP

(57) ABSTRACT

A fluid monitoring assembly includes a conduit having a wall defining a lumen for carrying fluid. A sensor mount is integrally formed with the wall of the conduit and extends generally transverse with respect to a longitudinal axis of the conduit, the sensor mount including an aperture defining an inner surface extending to the lumen. The assembly includes
(Continued)

a sensor configured to be removably secured within the sensor mount, the sensor having an elongate body terminating at one end thereof in a sensing portion, the elongate body having a male projection on a portion thereof and configured to rest within the inner surface of the sensor mount. The assembly further includes a housing having first and second portions connected to one another, the housing defining an interior portion configured to encapsulate the conduit, at least a portion of the elongate body of the sensor, and the sensor mount.

19 Claims, 14 Drawing Sheets

(51) Int. Cl.
*G01F 15/14* (2006.01)
*G01L 19/14* (2006.01)
*G01N 27/07* (2006.01)
*G01D 18/00* (2006.01)

(58) Field of Classification Search
USPC .................. 73/431, 886.5, 201, 198, 861
See application file for complete search history.

(56) References Cited

U.S. PATENT DOCUMENTS

| | | | |
|---|---|---|---|
| 4,840,068 A | 6/1989 | Mayhew, Jr. | |
| 5,197,708 A | 3/1993 | Campau | |
| 5,410,916 A | 5/1995 | Cook | |
| 5,549,134 A | 8/1996 | Browne et al. | |
| 5,713,388 A | 2/1998 | Brewer | |
| 6,012,339 A | 1/2000 | Genack et al. | |
| 6,036,166 A | 3/2000 | Olson | |
| 6,068,751 A | 5/2000 | Neukermans | |
| 6,280,408 B1 | 8/2001 | Sipin | |
| 6,543,483 B2 | 4/2003 | Johnson | |
| 6,554,589 B2 | 4/2003 | Grapes | |
| 6,631,736 B2 | 10/2003 | Seitz et al. | |
| 6,644,353 B1 | 11/2003 | Eidsmore | |
| 7,367,363 B2 | 5/2008 | Friedline et al. | |
| 7,788,047 B2 | 8/2010 | Schick et al. | |
| 7,857,506 B2 | 12/2010 | Schick et al. | |
| 7,861,608 B2 | 1/2011 | Furey et al. | |
| 7,927,010 B2 | 4/2011 | Schick et al. | |
| 8,235,067 B2 | 8/2012 | Gagne | |
| 8,302,496 B2 | 11/2012 | Furey et al. | |
| D671,853 S | 12/2012 | Furey et al. | |
| D684,076 S | 6/2013 | Furey et al. | |
| 8,506,162 B2 | 8/2013 | Schick et al. | |
| 8,656,951 B2 | 2/2014 | Gagne | |
| D710,226 S | 8/2014 | Furey | |
| 8,919,365 B2 | 12/2014 | Hillier et al. | |
| 9,181,941 B2 | 11/2015 | Cirou et al. | |
| 9,746,391 B2* | 8/2017 | Gagne | G01L 19/14 |
| 2004/0232923 A1 | 11/2004 | Farruggia et al. | |
| 2006/0020239 A1* | 1/2006 | Geiger | A61B 5/0031 604/9 |
| 2007/0058690 A1 | 3/2007 | Feldmeier et al. | |
| 2007/0139039 A1 | 6/2007 | Steinich | |
| 2007/0255527 A1 | 11/2007 | Schick et al. | |
| 2007/0295867 A1 | 12/2007 | Hennon | |
| 2008/0035227 A1 | 2/2008 | Woods et al. | |
| 2009/0120503 A1 | 5/2009 | Donahue | |
| 2009/0180513 A1 | 7/2009 | Schick | |
| 2009/0241677 A1 | 10/2009 | Klees et al. | |
| 2010/0288385 A1* | 11/2010 | Gagne | F16K 7/06 137/862 |
| 2011/0108136 A1* | 5/2011 | Margalit | G01F 1/06 137/343 |
| 2012/0242993 A1 | 9/2012 | Schick et al. | |
| 2013/0036844 A1* | 2/2013 | Furey | G01D 11/245 73/866.5 |
| 2013/0080081 A1 | 3/2013 | Dugger et al. | |
| 2013/0171265 A1 | 7/2013 | Saxena et al. | |
| 2013/0213130 A1 | 8/2013 | Ohmiya et al. | |
| 2013/0213140 A1 | 8/2013 | Eichhorn et al. | |
| 2013/0305839 A1 | 11/2013 | Muench et al. | |
| 2015/0013467 A1 | 1/2015 | Imai et al. | |
| 2016/0245714 A1* | 8/2016 | Gagne | G01N 27/10 |
| 2017/0322100 A1 | 11/2017 | Gagne | |

FOREIGN PATENT DOCUMENTS

| | | |
|---|---|---|
| CN | 204255565 U | 4/2015 |
| EP | 0522567 B1 | 10/1996 |
| WO | 97/26542 A1 | 7/1997 |
| WO | 2010/137392 A1 | 12/2010 |
| WO | 2012/143693 A1 | 10/2012 |
| WO | 2013/044195 A2 | 3/2013 |
| WO | 2013/125317 A1 | 8/2013 |

OTHER PUBLICATIONS

PCT International Search Report for PCT/US2014/062986, Applicant: Alphabio, Inc., Form PCT/ISA/210 and 220, dated Feb. 19, 2015 (4pages).
PCT Written Opinion of the International Search Authority for PCT/US2014/062986, Applicant: Alphabio, Inc., Form PCT/ISA/237, dated Feb. 19, 2015 (7pages).
BioWorks LLC Product Brochure (date: unknown), BSC: Bio Sample Cup, Safe, Sanitary Material Storage, Easton, PA 18042, www.BioWorksLLC.com (6 pages).
Parker Mitos Product Brochure, Mitos FREE FLOW Valve, Apr. 29, 2009, http://www.mitostech.com/freelow.html (2 pages).
PCT International Search Report for PCT/US10/34371, Applicant: AlphaBio, Inc., Form PCT/ISA/210 and 220, dated Jul. 1, 2010 (4 pages).
PCT Written Opinion of the International Search Authority for PCT/US10/34371, Applicant: AlphaBio, Inc., Form PCT/ISA/237, dated Jul. 1, 2010 (7 pages).
PCT International Preliminary Report on Patentability (Chapter I of the Patent Cooperation Treaty) for PCT/US2010/034371, Applicant: AlphaBio, Inc., Form PCT/IB/326 and 373, dated Nov. 15, 2011 (9 pages).
PCT International Search Report for PCT/US15/011791, Applicant: Alphinity, LLC, Form PCT/ISA/210 and 220, dated Apr. 10, 2015 (4 pages).
PCT Written Opinion of the International Search Authority for PCT/US15/011791, Applicant: AlphaBio, Inc., Form PCT/ISA237, dated Apr. 10, 2015 (7 pages).
The extended European search report dated Aug. 8, 2017 in European Patent Application No. 15737630.2, (10pages).
Communication pursuant to Rules 70(2) and 70a(2) EPC dated Aug. 25, 2017 in European Patent Application No. 15737630.2, (1page).
Supplementary Search Report dated May 15, 2017 in European Patent Application No. 14 85 7877, (10pages).
Supplementary Search Report dated Feb. 28, 2018 in European Patent Application No. 14 85 7877, (8pages).
Communication pursuant to Article 94(3) EPC dated Dec. 6, 2017 in European Patent Application No. 14 85 877, (4pages).
Notification of the First Office Action dated Aug. 27, 2018 in Chinese Patent Application No. 2015800141676, Applicant: Alphinity, LLC, (19 pages).
Examination report No. 1 for standard patent application dated Nov. 15, 2018 in Chinese Patent Application No. 2015206311, Applicant: Alphinity, LLC, (3pages).

* cited by examiner

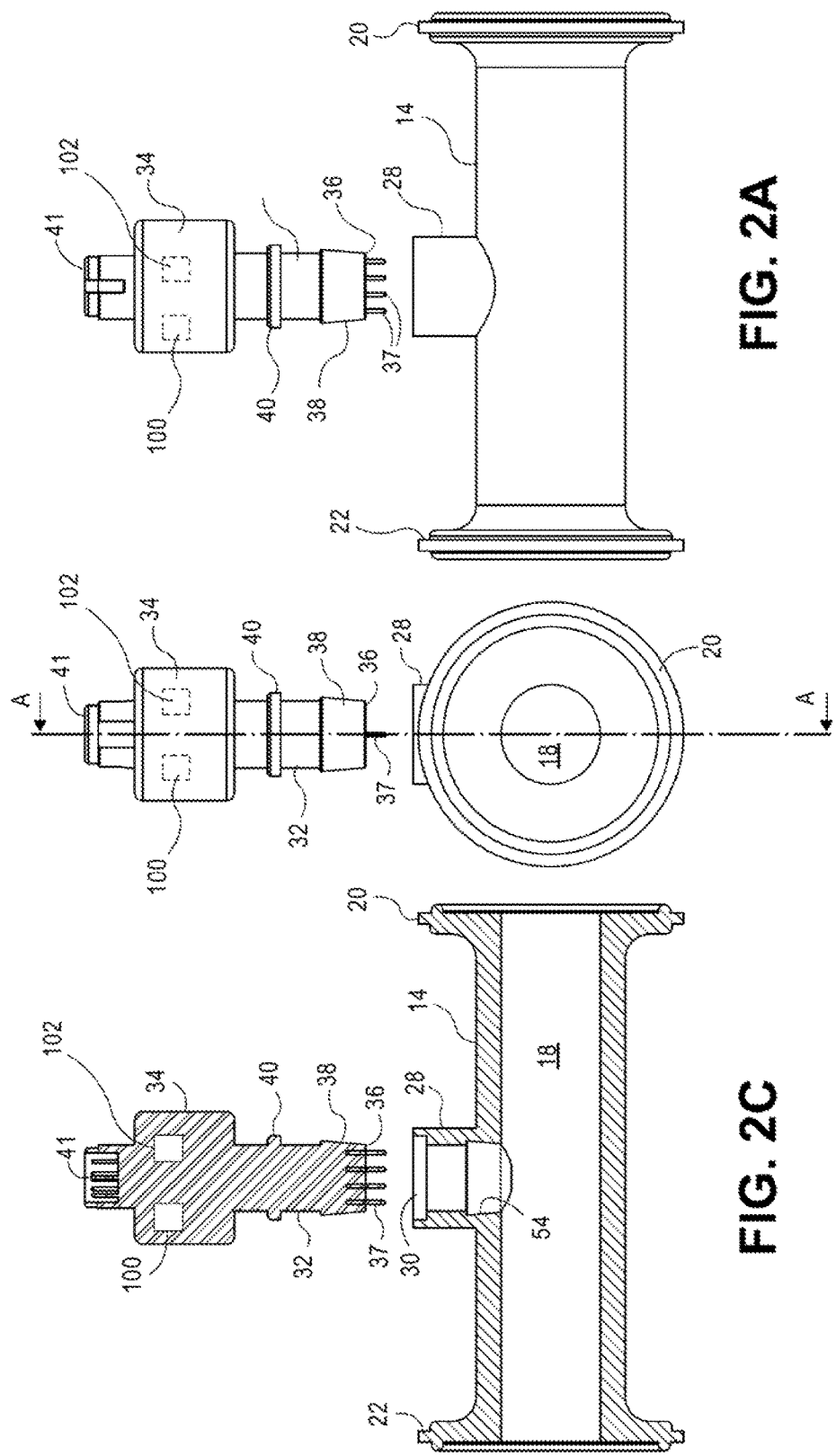

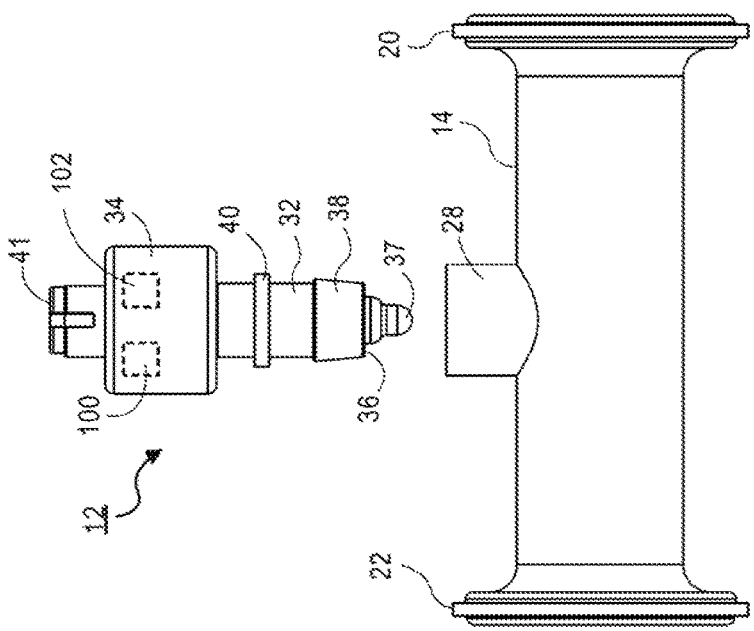
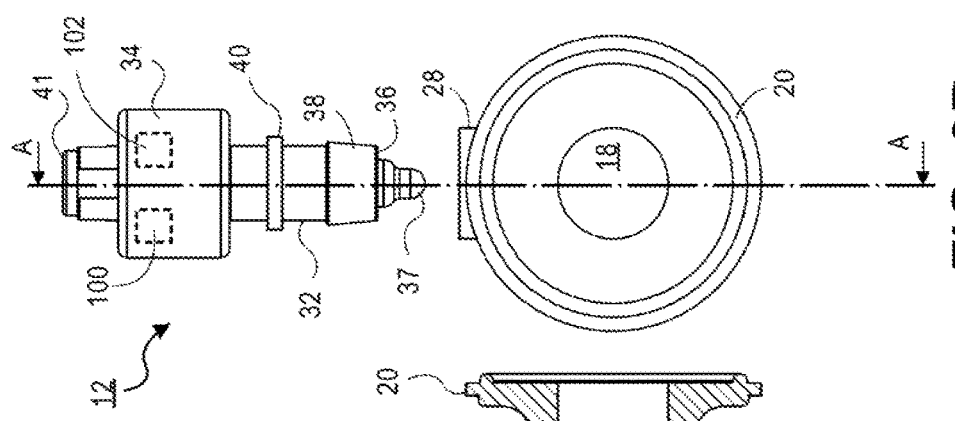
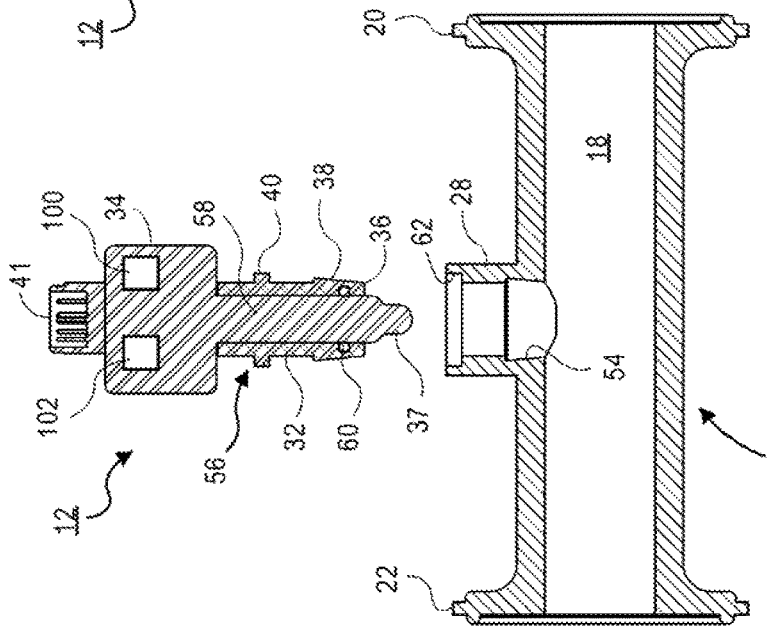
FIG. 3A
FIG. 3B
FIG. 3C

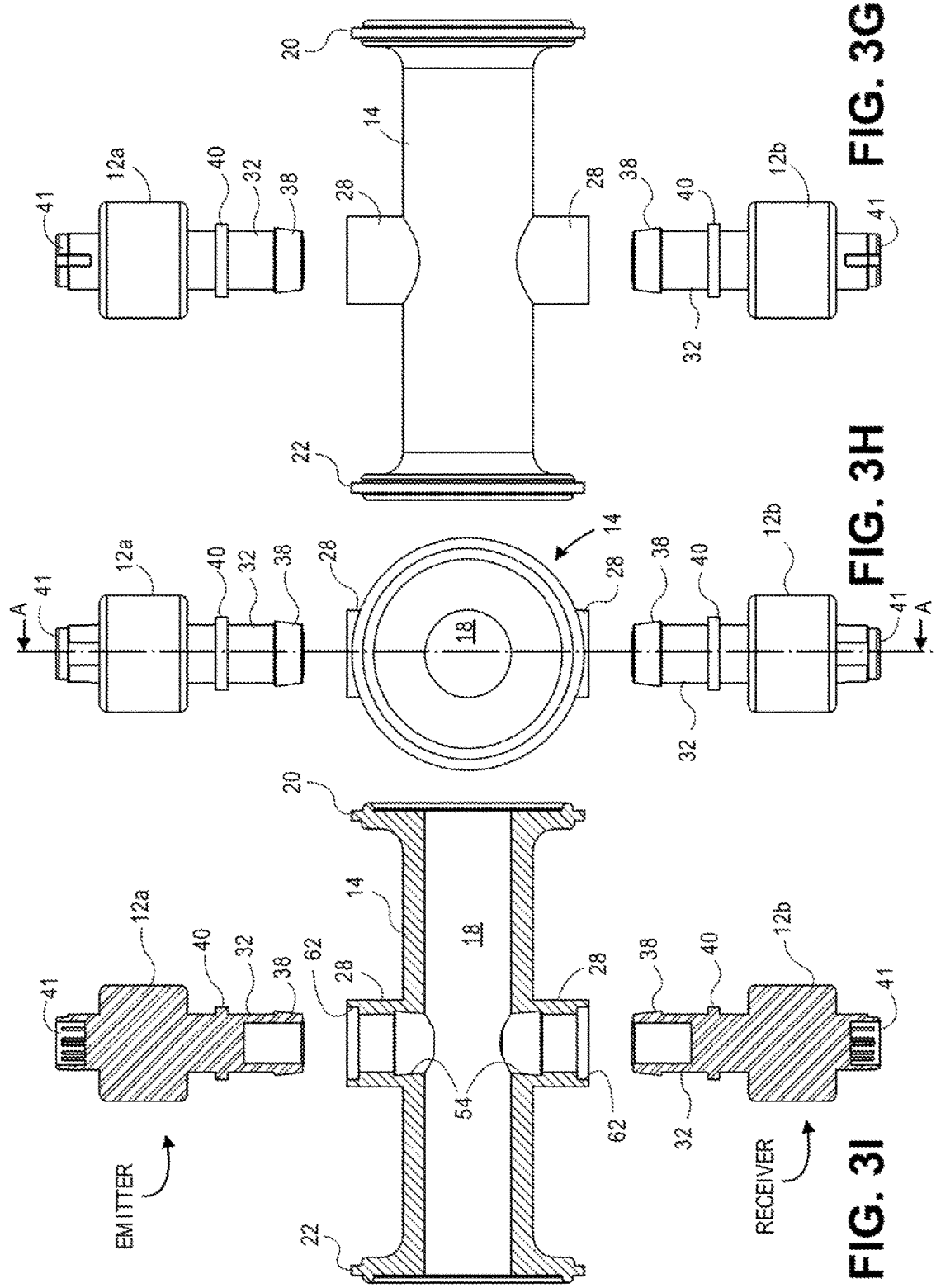

SECTION A-A

FLUID MONITORING ASSEMBLY WITH SENSOR FUNCTIONALITY

RELATED APPLICATION

This Application is a U.S. National Stage filing under 35 U.S.C. § 371 of PCT Patent Application No. PCT/US2015/011791, filed Jan. 16, 2015, which claims priority to U.S. Provisional Patent Application No. 61/928,905 filed on Jan. 17, 2014. The contents of the aforementioned applications are incorporated by reference herein. Priority is expressly claimed in accordance with 35 U.S.C. §§ 119, 120, 365 and 371 and any other applicable statutes.

FIELD OF THE INVENTION

The field of the invention generally relates to fluid monitoring devices and, in particular segments of conduit or tubing that incorporate sensor functionality. More specifically, the invention pertains to connectors, valves, or interfaces used by pharmaceutical and biological applications or other hygienic process industries that include sensors therein.

BACKGROUND

Many commercial products are produced using chemical as well as biological processes. Pharmaceuticals, for example, are produced in commercial quantities using scaled-up reactors and other equipment. So-called biologics are drugs or other compounds that are produced or isolated from living entities such as cells or tissue. Biologics can be composed of proteins, nucleic acids, or complex combinations of these substances. They may even include living entities such as cells. In order to produce biologics on a commercial scale, sophisticated and expensive equipment is needed. In both pharmaceutical and biologics, for example, various processes need to occur before the final product is obtained. For example, in the case of biologics, cells may be grown in a growth chamber or the like and nutrients may need to be carefully modulated into the growth chamber. Waste products produced by cells may also have to be removed on a controlled basis from the fermentation chamber. As another example, biologic products produced by living cells or other organisms may need to be extracted and concentrated. This process may involve a variety of filtration and separation techniques.

Because there are a number of individual processes required to be produce the final product, various reactants, solutions, and washes are often pumped or otherwise transported to various subsystems using conduits and associated valves. These systems may be quite cumbersome and organizationally complex due to the large numbers of conduits, valves, sensors, and the like that may be needed in such systems. Not only are these systems visually complex (e.g., resembling spaghetti) they also include many components that are required to be sterilized between uses to avoid cross-contamination issues. Indeed, the case of drug and biologic preparation, the Federal Food and Drug Administration (FDA) is becoming increasingly strict on cleaning, sterilization or bio-burden reduction procedures that are required for drug and pharmaceutical preparations. This is particularly of a concern because many of these products are produced in batches which would require repeated cleaning, sterilization or bio-burden reduction activities on a variety of components.

During the manufacturing process of pharmaceuticals and biologics there often is a need to incorporate sensors into the manufacturing process so that process variables are monitored. For example, the process variables that need to be monitored may include temperature, pressure, pH, conductivity, and the like. In conventional setups, sensors are placed directly along one or more points of the production process whereby the sensors themselves are inserted into the production stream where the sensor makes direct contact with the reactant or product stream. In conventional manufacturing processes, the sensors may need to be changed, for example, due to a malfunction or because the product being manufactured requires a different sensor. In these examples, it can be a time consuming and expensive process to replace these sensors and also ensuring that reactants or products remain uncontaminated.

SciLog BioProcessing Systems, for example, produces a line of single use disposable sensors for use with bioprocessing applications. These include pressure sensors, temperature sensors, and conductivity sensors. In the SciLog sensors, the entire unit is thrown away including the tubing, sensor, and associated housing. U.S. Pat. No. 7,788,047, for example, discloses a disposable, pre-calibrated, pre-validated sensor for use in bio-processing applications. A problem with the SciLog single-use sensors is that the sensors include an integrated segment of conduit. This integrated segment of conduit adds unnecessary dead volume wherein product may reside. Moreover, the SciLog single-use sensors are available only in a few sizes.

SUMMARY

According to one embodiment of the invention, a fluid monitoring assembly includes a conduit having a wall defining a lumen through which the fluid passes and a sensor mount integrally formed with the wall of the conduit and extending generally transverse with respect to a longitudinal axis of the conduit, the sensor mount including and aperture that defines an inner surface that extends into the main lumen of the conduit. The inner surface of the surface mount may include a circumscribing inner recess. The assembly includes a sensor configured to be removably secured within the sensor mount, the sensor having an elongate body terminating at one end thereof in a sensing portion, the elongate body having a male projection on a portion thereof and configured to rest within the inner surface of the sensor mount (or in some embodiments, an inner recess formed on the inner surface) when secured within the sensor mount. The elongate body, in some embodiments, has a flange portion configured to rest within a seat on the sensor mount. The fluid monitoring assembly includes a housing or jacket having first and second portions connected to one another at a hinge, the housing defining an interior portion configured to encapsulate the conduit, at least a portion of the elongate body of the sensor, and the sensor mount. The housing or jacket provides resistance to high fluid pressures contained within the conduit.

In another embodiment of the invention, a fluid monitoring assembly includes a conduit comprising a wall defining a lumen through which the fluid passes and a sensor mount integrally formed with the wall of the conduit and extending generally transverse with respect to a longitudinal axis of the conduit, the sensor mount including an aperture formed therein and an inner surface extending from the aperture to the main lumen. The fluid monitoring assembly includes a sensor configured to be removably secured within the sensor mount, the sensor having an elongate body terminating at one end thereof in a sensing portion, the elongate body having a male projection on a portion thereof and configured to rest within the inner recess when secured within the sensor mount. The fluid monitoring assembly includes a housing having first and second portions, wherein an interior portion of the first and second portions are configured to encapsulate the conduit, at least a portion of the elongate body of the sensor, and the sensor mount. One or more pinch valves are disposed on the housing and configured to selectively pinch the conduit to modulate flow therein. When pinched, fluid flow through the pinch point is prevented. When un-pinched, fluid flows through the conduit unimpeded.

In another embodiment, a method of directing flow in a fluid monitoring assembly that includes a conduit comprising a wall defining a lumen through which the fluid passes, a sensor mount integrally formed with the wall of the conduit and extending generally transverse with respect to a longitudinal axis of the conduit, the sensor mount including an aperture defining an inner surface extending through the sensor mount to the lumen. The sensor is configured to be removably secured within the sensor mount, the sensor having an elongate body terminating at one end thereof in a sensing portion, the elongate body having a male projection on a portion thereof and configured to rest within the inner recess when secured within the sensor mount. The fluid monitoring assembly includes a housing configured to encapsulate the conduit, at least a portion of the elongate body of the sensor, and the sensor mount. The fluid monitoring assembly includes one or more pinch valves disposed on the housing and configured to pinch the conduit. The method includes sensing a parameter with the sensor and detecting when the parameter passes a threshold value, and actuating the one or more pinch valves to adjust flow with the conduit. As one example, the one or more pinch values shunts flow to a bypass conduit.

In another embodiment of the invention, a method of changing a fluid monitoring assembly is disclosed in which the fluid monitoring assembly includes a conduit comprising a wall defining a lumen through which the fluid passes, a sensor mount integrally formed with the wall of the conduit and extending generally transverse with respect to a longitudinal axis of the conduit, the sensor mount including an aperture and inner surface extending from the aperture to the main lumen. The assembly includes a sensor configured to be removably secured within the sensor mount, the sensor having an elongate body terminating at one end thereof in a sensing portion, the elongate body having a male projection on a portion thereof and configured to rest within inner surface of the surface mount. The fluid monitoring assembly further including a housing configured to encapsulate the conduit, at least a portion of the elongate body of the sensor, and the sensor mount. The method includes opening the housing, removing the at least one of the sensor and the conduit, inserting a replacement for the at least one of the sensor and conduit, and closing the housing.

BRIEF DESCRIPTION OF THE DRAWINGS

FIG. 2A is a side view of a conductivity sensor and associated conduit according to one embodiment.

FIG. 2B illustrates an end view of the conductivity sensor and conduit of FIG. 2A.

FIG. 2C illustrates a cross-sectional view of the sensor and conduit taken along the line A-A of FIG. 2B.

FIG. 3A illustrates a side view of a pH sensor and associated conduit according to one embodiment.

FIG. 3B illustrates an end view of a sensor and conduit of FIG. 3A.

FIG. 3C illustrates a cross-sectional view of the sensor and conduit taken along the line A-A of FIG. 3B.

FIG. 3G illustrates a side view of a pressure sensor and associated conduit according to one embodiment.

FIG. 3H illustrates an end view of a sensor and conduit of FIG. 3G.

FIG. 3I illustrates a cross-sectional view of the sensor and conduit taken along the line A-A of FIG. 3H.

DETAILED DESCRIPTION OF THE ILLUSTRATED EMBODIMENTS

Figure 1:
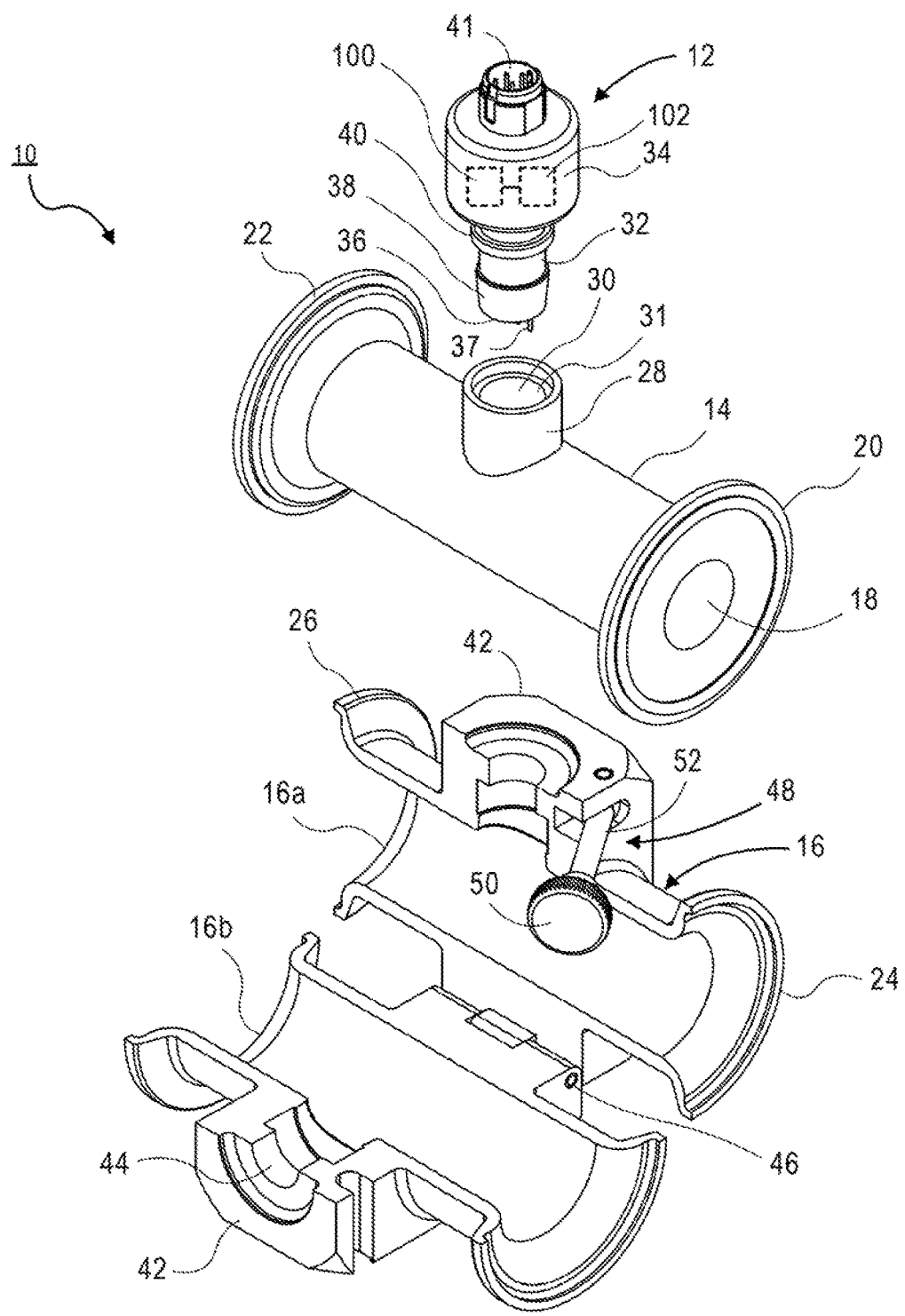
FIG. 1 illustrates an exploded perspective view of a fluid monitoring assembly according to one embodiment.

FIG. 1 illustrates one embodiment of a fluid monitoring assembly 10 according to one embodiment. The fluid monitoring assembly 10 includes a sensor 12 that can be removably inserted into a conduit 14. The conduit 14 may be designed as a length of unreinforced tubing in which a lumen 18 is defined by a wall of the conduit 14. The fluid monitoring assembly 10 further includes a two-part housing 16 that is used to encapsulate the conduit 14 and at least a portion of the sensor 12 when the sensor 12 is mounted therein. The two-part housing 16 acts as jacket that surrounds the conduit 14 and part of the sensor 12 contained therein. The two-part housing or jacket 16 defines an exoskeleton-type structure that surrounds the unreinforced polymer conduit 14 and prevents the unreinforced polymer conduit 14 from failing (e.g., bursting or forming an aneurysm type bulge in the conduit) under high fluid pressures.

The fluid monitoring assembly 10 can handle significant fluid pressures by using the encapsulated construction. For example, the fluid monitoring assembly 10 can withstand pressures exceeding 100 psi in some applications without damage or failure.

The conduit 14 includes the lumen 18 extending between opposing ends through which fluid passes. For example, one end of the conduit 14 may be an inlet to the fluid monitoring assembly 10 while the opposing end of the conduit 14 may be an outlet to the fluid monitoring assembly 10. The conduit 14 terminates at opposing ends with flanges 20, 22. In some alternative embodiments, the conduit 14 may not terminate in flanges as illustrated. In the embodiment of FIG. 1, the housing 16 includes respective receiving flange portions 24, 26 that are dimensioned to receive the flanges 20, 22 of the conduit 14 when the housing 16 is closed about the conduit 14. The conduit 14 may be formed as a cylindrical segment of tubing although other geometries are contemplated. The receiving flanges 24, 26 are designed to mate with corresponding flanges (not shown) contained in fluid line of a manufacturing process. In this regard, the fluid monitoring assembly 10 may be inserted at desired locations so that the sensor 12 may be easily added or removed as necessary. Typically, the respective facing surfaces of the flanges 24, 26 (and opposing ends) are held together via a clamp or the like such as the clamp or collar 76 that is illustrated, for example, in FIGS. 5A and 5B. An o-ring or other seal (not shown) may be provided in a groove contained in the flanges 24, 26 for sealing purposes.

The conduit 14 may be made from a polymer material. Examples of materials usable for the conduit 14 include, by way of example, thermoplastic elastomers (TPE), thermoplastic rubber (TPR), silicone (thermally or UV-cured), or other polymers. Referring to FIG. 1, the conduit 14 contains a sensor mount 28 integrally formed with the wall of the conduit 14 and extending generally transverse with respect to a longitudinal axis of the conduit 14. The sensor mount 28 includes an aperture 30 that defines and opening to an inner surface of the sensor mount 28 that receives a portion of the sensor 12 as explained in more detail herein. The sensor 12 includes elongate body portion 32 that extends from a base 34. The elongate body portion 32 may be a shank or the like that extends away from the base 34. The elongate body portion 32 terminates at a sensing end 36. The sensing end 36 includes the various sensing elements 37 that are used to sense a particular parameter being measured by the sensor 12. An aperture is provided in the wall of the conduit 14 such that that the sensing element(s) 37 has direct access to the fluid passing through the lumen 18 of the conduit 14. In other embodiments (e.g., pressure sensor 12), the sensing element(s) 37 may not need direct contact with fluid passing through the lumen 18 of the conduit 14. The particular make-up of the sensing element 37 depends on the sensor 12 being used. For example, the sensing element 37 may include electrodes or pins in the case where the sensor 12 is a conductivity sensor. The sensing element 37 may include a diaphragm or strain gauge when the sensor 12 is pressure sensor. The sensing element 37 may include a thermistor or thermocouple when the sensor 12 is a temperature sensor. The sensing element 37 may include a porous glass membrane or the like when the sensor 12 is a pH sensor. The elongate body portion 32 includes a male projection or end 38 located near the sensing end 36 of the sensor 12. The male projection 38 may include a barbed end as is shown in FIG. 1. Still referring to FIG. 1, the elongate body portion 32 may also include a flange 40 that extends radially away from the elongate body portion 32. In this particular embodiment, the flange 40 is located on the elongate body portion 32 such that when the sensor 12 is inserted into the conduit 14, the flange 40 rests atop the upper portion of the mount 28 (e.g., a seat within the upper portion of the sensor mount 28 that is dimensioned to receive the flange 40). As described herein in more detail, the male projection 38 on the sensor 12 interfaces with a correspondingly "female" shaped inner recess 31 that circumscribes an inner surface of the sensor mount 28. The base 34 of the sensor 12 may include a connector 41 that connects to cabling or other wiring (not shown) that transmits data from the sensor 12 to a reading device or transmitter (not shown). The connector 41 may include a DIN type pin connector as is shown in FIG. 1 although other connector types are contemplated.

The housing 16 includes a reinforced portion 42 that is oriented generally perpendicular to the long axis of the orientation of the conduit 14 within the housing 16 and defines a bore 44 when the two halves of the housing 16 are brought together. The bore 44 is dimensioned and configured to closely encapsulate the mount 28 as well as a portion of the elongate body portion 32 of the sensor 12. In one preferred embodiment, the housing 16 is typically made from a polymer material such as plastic materials. Materials include standard thermoplastics and polyolefins such as polyethylene (PE) and polypropylene (PP) or a hard plastic such as polyetherimide (PEI) such as ULTEM resins. The housing 16 may also be formed from fluoropolymers such as polyvinylidene fluoride (PVDF) or perfluoroalkoxy (PFA), polytetrafluoroethylene (PTFE), polycarbonate (which may be more thermally resistant), polysulfone (PSU), and the like. The housing 16 may also be made of metals. The two-part housing 16 includes a first half 16a and a second half 16b that are connected together via a hinge 46. The hinge 46 may be constructed, for example, as a rod, post, or pin that is contained within an aperture or bore within the housing 16 that permits the first half 16a and second half 16b to pivot from a closed state to an open state so that the conduit 14 and the sensor 12 can be easily removed and replaced. A fastener 48 such as a locking knob 50 and associated hinged, locking arm 52 can be used to fixedly hold the two-part housing 16 in the closed state. The locking arm 52 may be threaded and the locking knob 50 contains corresponding threads and can be tightened or loosened by rotation of the knob 50. To close the housing 16, the locking arm 52 is rotated within a groove contained on the second half 16b of the housing 16 and the knob 50 is tightened to secure the first half 16a securely to the second half 16b of the housing 16. Of course, other types of fasteners 48 can be used in place of or in conjunction with the locking arm 52 and knob 50. These include screws, nuts, clamps, bands, ties, and the like.

Still referring to FIG. 1, the sensor 12 may optionally have contained therein or integrated therein a memory 100. The memory 100 may include a volatile or non-volatile memory. One example of memory 100 that may be used in connection therewith includes EEPROM and flash memory. In one embodiment, the memory 100 is located on or associated with circuitry 102 that resides in the base 34 although the particular physical location of the memory 100 may vary. In one preferred aspect, the memory 100 stores information related to the individual sensor 12 and, as explained in more detail below, at least some calibration information relating to the sensor 12. The stored information may include a serial number for the sensor, a manufacturing date, lot ID, a calibration date, and a plurality of calibration points. The multiple calibration points are used to ensure that a particular parameter (e.g., pressure, temperature, pH, conductivity)

may be measured by the sensor 12. The memory 100 and circuitry 102 are optional and are illustrated as being incorporated into the embodiments illustrated in FIGS. 2A-2C, 3A-3F, 4A-4D, and 5A-5F.

FIG. 2A illustrates a side view of a conduit 14 and a sensor 12. Note that the conduit 14 and the sensor 12 in this embodiment share similar reference numbers as those used in FIG. 1 for common features found in both embodiments. In this example, the sensor 12 is a conductivity sensor and the sensing elements 37 include a plurality of electrode pins that project from the sensing end 36 of the sensor 12. FIG. 2B illustrates an end view of the same segment of conduit 14 and sensor 12. FIG. 2C illustrates a cross-sectional view of the sensor 12 and the conduit 14 taken along the line A-A of FIG. 2B. As best seen in FIG. 2C, the inner surface of the sensor mount 28 includes "female" shaped inner recess 54 that circumscribes the entire inner surface. The inner recess 54 is dimensioned in size and geometry to closely engage with the male projection 38 of the sensor 12. That is to say, in one preferred embodiment, the inner recess 54 has a profile that closely matches that of the male projection or barb 38. The angles or slope of the inner recess 54 may be the same as the angle or slope of the male projection or barb 38. In this configuration, when the sensor 12 is inserted into the conduit 14, the male projection 38 engages with the female inner recess 54 and the flange 40 rests atop the upper surface of the sensor mount 28 or within a recessed seat of the mount as seen in FIG. 3F, for example. In this embodiment, the sensing elements 37 (e.g., pins) extend into the lumen 18 of the conduit 14 and are in direct contact with fluid passing therein. The sensor 12 may be removed from the conduit 14 by pulling the sensor 12 proximally relative to the conduit 14. In this regard, the sensor 12 may be removably secured to the conduit 14. For example, the conduit 14 may be replaced by pulling the sensor 12 out of the pre-existing conduit 14 and inserting this same sensor 12 into a new segment of conduit 14. Alternatively, the sensor 12 may be pulled out of the pre-existing conduit 14 and replaced with another sensor 12. In still another alternative, both the conduit 14 and the sensor 12 may be replaced. While not specifically illustrated in FIGS. 2A-2C, the conduit 14 and sensor 12 may include an encapsulating housing 16 similar to that described in the context of FIG. 1. The encapsulating housing 16 would have first and second halves 16a, 16b and be constructed to mate with the geometrical profile of the conduit 14 and sensor 12.

Figure 3D:
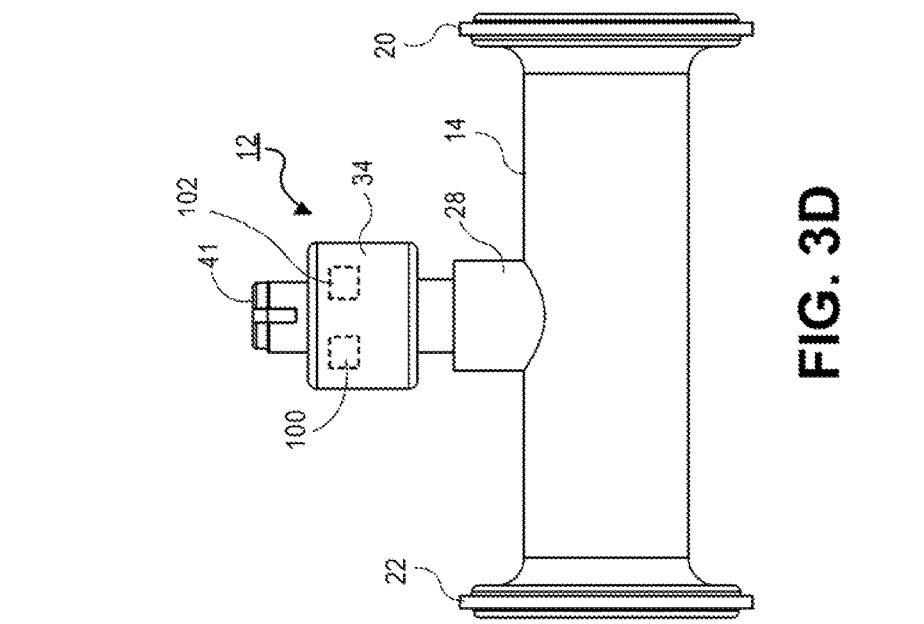
FIG. 3D illustrates a side view of a pH sensor and associated conduit according to one embodiment.
Figure 3E:
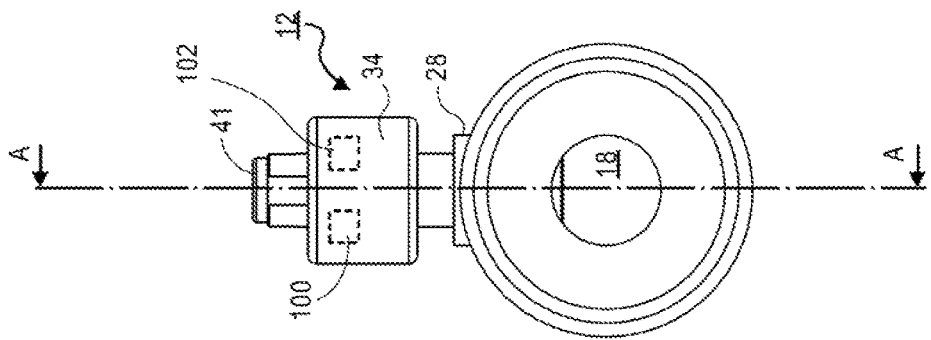
FIG. 3E illustrates an end view of a sensor and conduit of FIG. 3D.
Figure 3F:
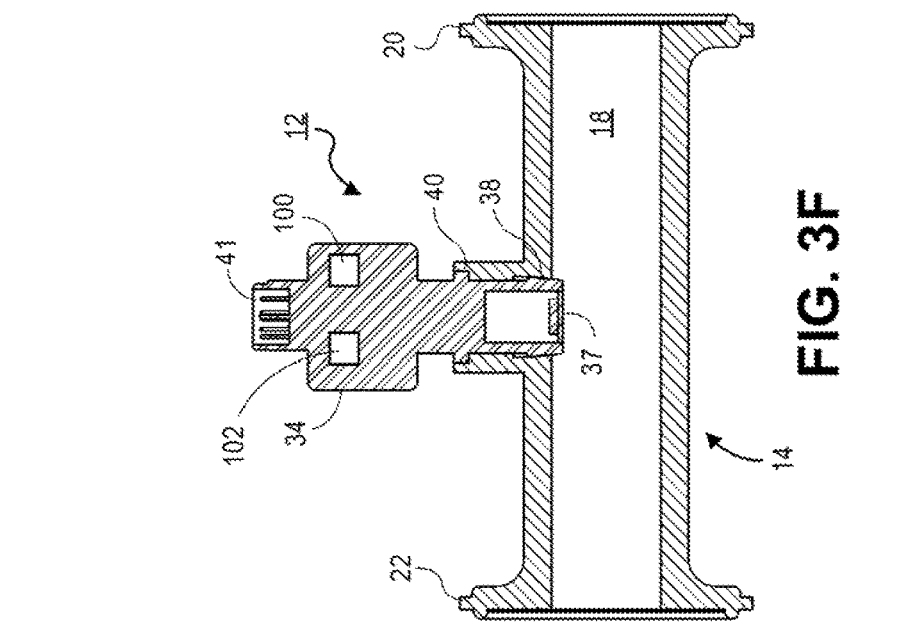
FIG. 3F illustrates a cross-sectional view of the sensor and conduit taken along the line A-A of FIG. 3E.

FIGS. 3A-3C illustrate an embodiment of a sensor 12 that measures pH. Again, note that the conduit 14 and the sensor 14 in this embodiment share similar reference numbers as those used in FIG. 1 for common features found in both embodiments. In this embodiment, the sensing element 37 may include a glass permeable electrode or similar element that is exposed to the lumen 18 of the conduit 14. In this embodiment, the male projection 38 and the flange 40 may be part of an insert 56 that is positioned over the shank 58 of a pH sensor 12. Further, the insert 56 may include a recess for holding a seal 60 that is interposed between an inner surface of the insert 56 and an outer surface of the shank 58 to prevent fluid infiltration. As seen in FIG. 3C, the upper surface of the sensor mount 28 may include a circumferential seat 62 that is dimensioned to receive the flange 40 of the sensor 12. As an alternative to the seat 62, the flange 40 may just rest atop an upper surface of the sensor mount 28. In still another alternative, the flange 40 may be omitted entirely. FIGS. 3D, 3E, and 3F illustrate yet another embodiment of a sensor 12 in the form of a pressure sensor. Again, note that the conduit 14 and the sensor 14 in this embodiment share similar reference numbers as those used in FIG. 1 for common features found in both embodiments. This sensor 12 is used to measure pressure. The sensing element 37 may include a diaphragm or strain gauge or other pressure sensing element. As seen in FIG. 3F, the sensing element 37 projects somewhat into the lumen 18 of the conduit 14. In this embodiment, the flange 40 of the sensor 12 is illustrated as resting within the circumferential seat 62 on the mount 28. FIGS. 3G-3I illustrate an embodiment wherein the sensor 12 is a UV sensor that is used to detect and/or measure the concentration of various chemical species contained in the fluid. Features of the conduit 14 and sensor 12 in this embodiment share similar reference numbers as those used in FIG. 1 for common features found in both embodiments. While not specifically illustrated in FIGS. 3A-3I, the conduit 14 and sensor 12 may include an encapsulating housing 16 similar to that described in the context of FIG. 1. The encapsulating housing 16 would have first and second halves 16a, 16b and be constructed to mate with the geometrical profile of the conduit 14 and sensor 12.

The UV sensor 12 may be used to detect and/or measure constituents within the fluid which may include, by way of example, proteins, enzymes, and the like that have unique UV absorbance characteristics. The UV sensor 12 may also be used to measure the turbidity of a fluid that runs through the lumen 18 of the conduit 14. In this embodiment, the sensor 12 is broken into an emitter portion 12a and a receiver portion 12b. The receiver portion 12a emits ultraviolet radiation (e.g., light at a wavelength within the UV spectrum such as 280 nm) that is transmitted transversely through the fluid flowing in the lumen 18. The transmitted light is collected at the receiver portion 12b. The degree of light transmission is used to detect and/or quantify chemical species contained in the fluid within the lumen 18 of the conduit 14. The emitter portion 12a and the receiver portion 12b are inserted into the conduit 14 at opposing locations across a segment of the conduit 14. As seen in FIG. 3I, both the emitter portion 12a and the receiver portion 12b include the male ends 38 and flanges 40 that interface with corresponding seats 62 in the sensor mounts 28. It should be understood, however, that in some alternative embodiments, only one of the emitter portion 12a or the receiver portion 12b may have the male end 38 or flange 40.

Figure 4A:
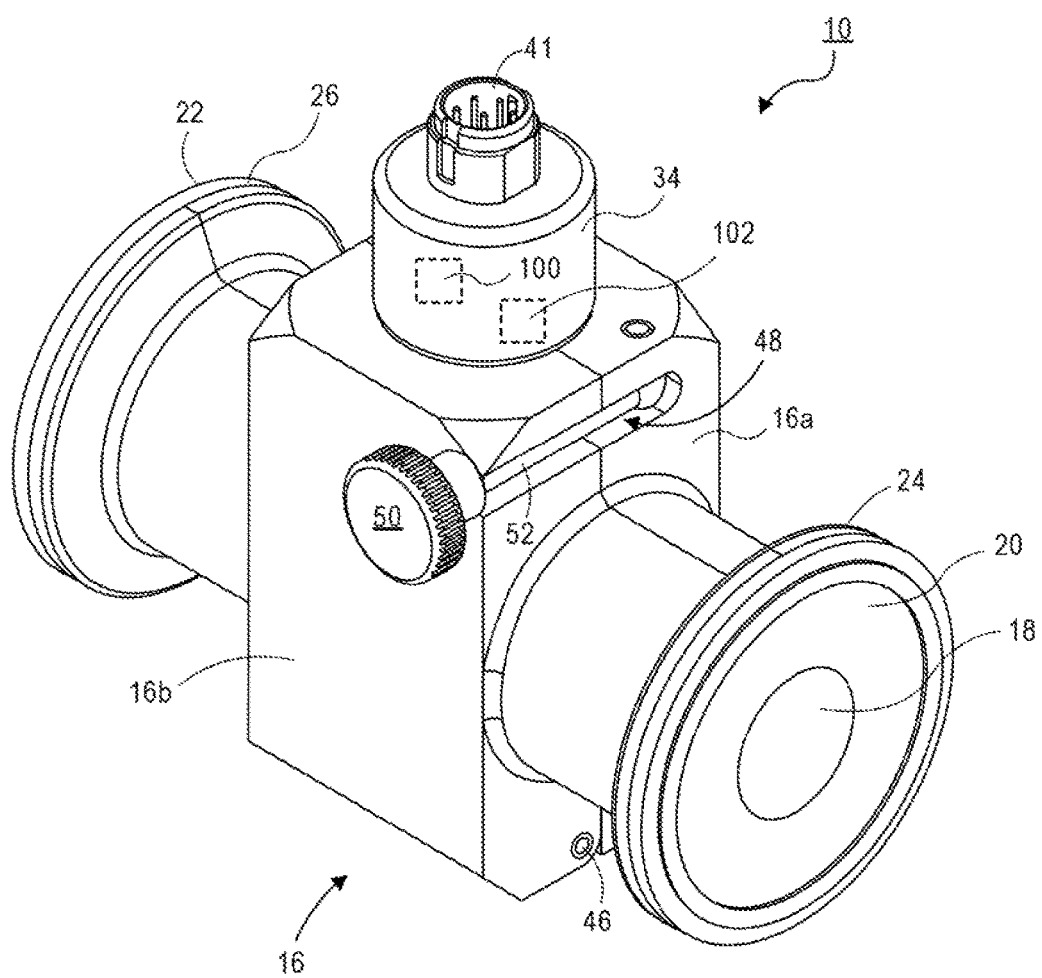
FIG. 4A illustrates a perspective view of the fluid monitoring assembly fully enclosed in the housing according to one embodiment.
Figure 4B:
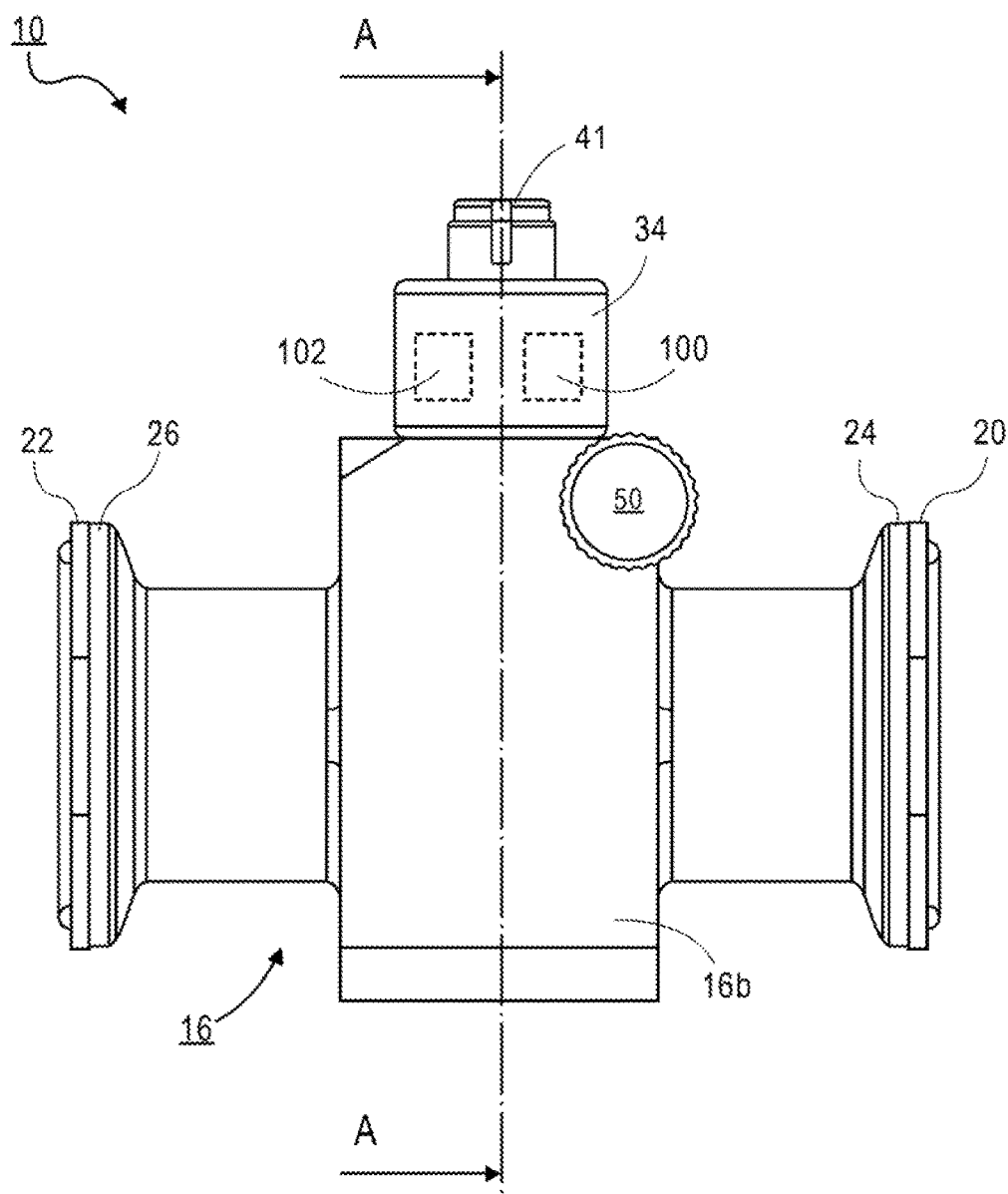
FIG. 4B illustrates a side view of the fluid monitoring assembly of FIG. 4A.
Figure 4C:
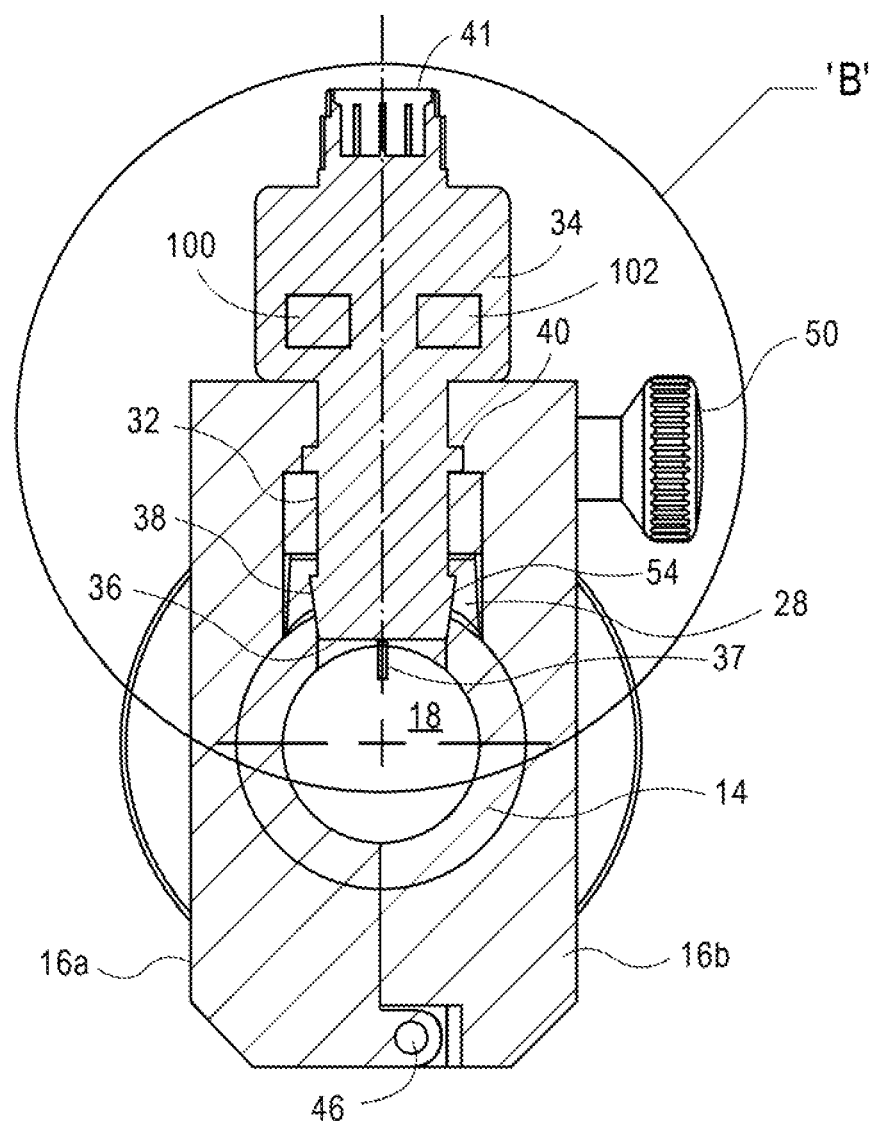
FIG. 4C illustrates a cross-sectional view of the fluid monitoring assembly taken along the line A-A of FIG. 4B.
Figure 4D:
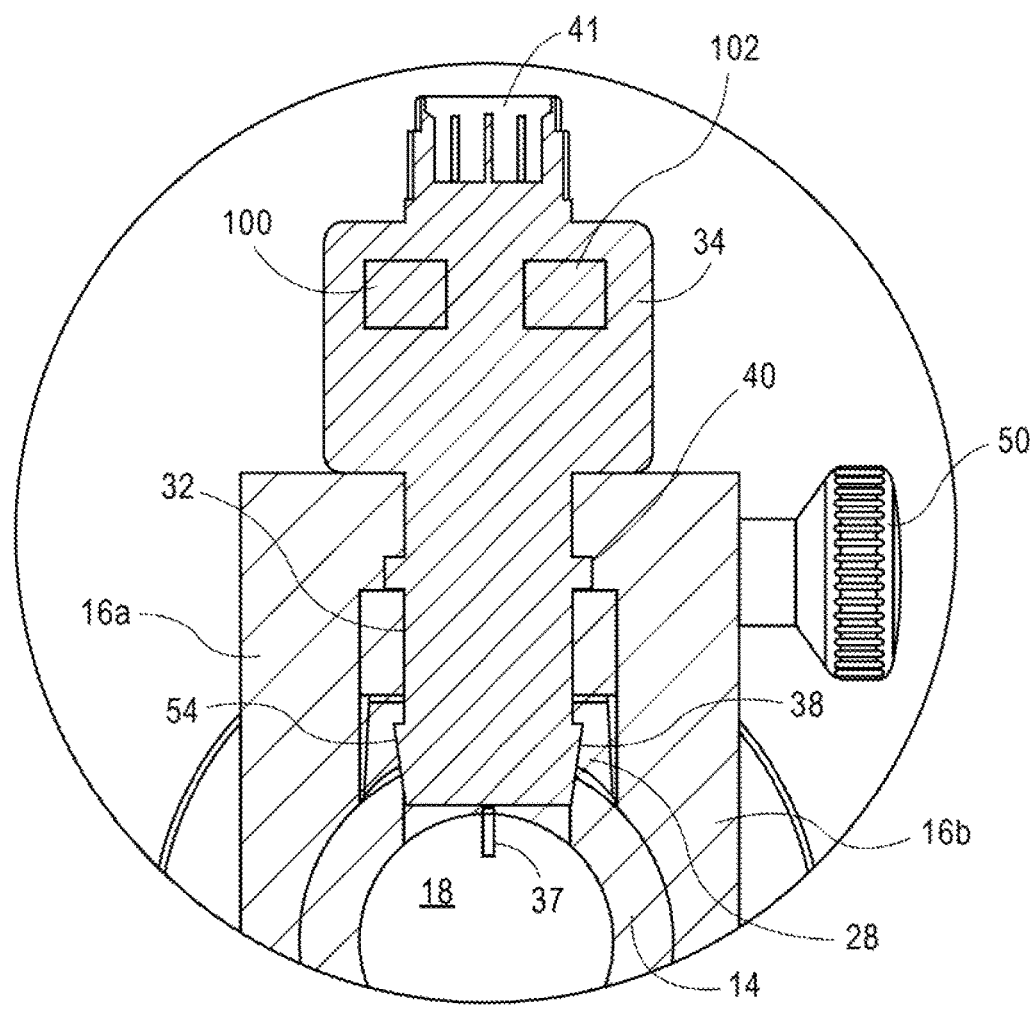
FIG. 4D illustrates a detailed view of detail B of FIG. 4C.

FIGS. 4A-D illustrates an embodiment of a sensor 12 in the form of a conductivity sensor that is fully enclosed within a housing 16 along with the conduit 14. Features of the conduit 14 and sensor 12 in this embodiment share similar reference numbers as those used in FIG. 1 for common features found in both embodiments. FIG. 4A illustrates a perspective view of the fluid monitoring assembly 10 where the two-part housing 16a, 16b is in the closed state. The locking arm 52 is rotated to slide within a slot 51 formed within the first half 16a and the second half 16b of the housing 16. The knob 50 is tightened on the locking arm 52 to pinch and hold the two halves 16a, 16b together around the conduit 14 and at least a portion of the sensor 12. The two halves 16a, 16b thus serve to jacket the conduit 14 and enables the conduit 14 to carry very high pressures of fluid without the need for the conduit 14 to be reinforced (e.g., braided). FIG. 4B illustrates a side view of the fluid monitoring assembly 10. Note that in this embodiment, the conduit 14 terminates at respective flanges 20, 22 that are contained within corresponding flanges 24, 26 formed in the housing 16. FIG. 4C illustrates a cross-sectional view of the fluid monitoring assembly 10 taken along the line A-A of FIG. 4B. As seen in FIG. 4C, the sensing element 37 projects into the interior of the lumen 18 such that fluid can contact the sensing element 37. As seen in FIG. 4C, a male projection 38 in the shape of a barb engages with the inner recess 54 contained in the sensor mount 28. FIG. 4D is a detailed view of detail B of FIG. 4C. Referring to FIGS. 4C and 4D note how the housing portions 16a, 16b closely matches the contours of the sensor mount 28 and the elongate body portion 32 of the sensor 12 with parts of the housing portions 16a, 16b being configured with recesses or the like to encapsulate and maintain the position of the sensor 12 within the conduit 14. The sensor 12 cannot be pushed or pulled out of the conduit 14 as it is being rigidly held in place by the housing 16 jacketing the conduit 14 and a portion of the senor 12. Both the male end 38 of the sensor 12 and the flange 40 aid in preventing the sensor 12 from escaping from the conduit 14 from, for example, high pressures. Multiple flanges 40 may be used to add further robustness to the design.

Figure 5A:
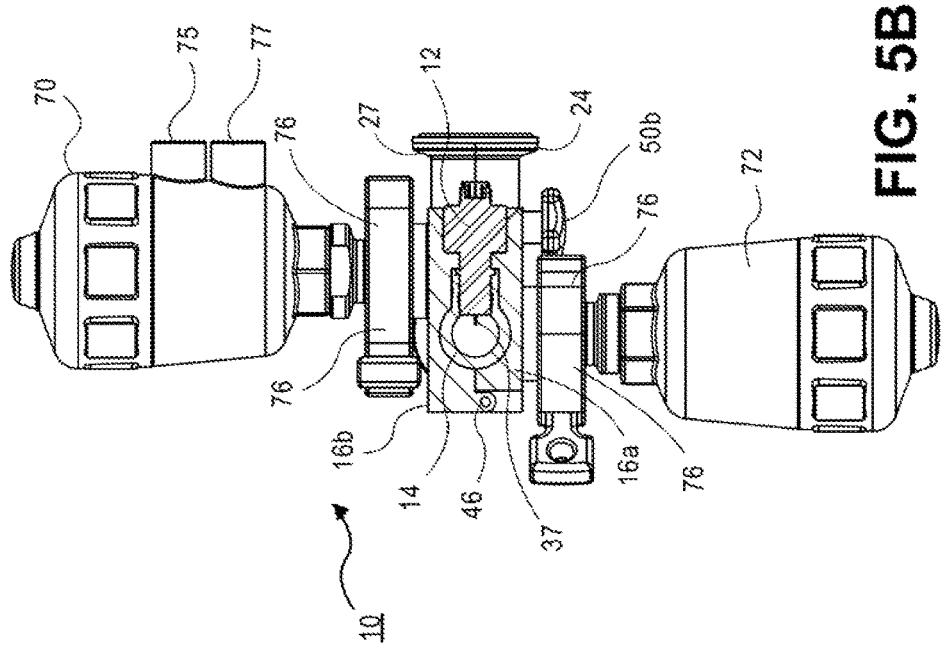
FIG. 5A illustrates a side view of a fluid monitoring assembly according to another embodiment.
Figure 5B:
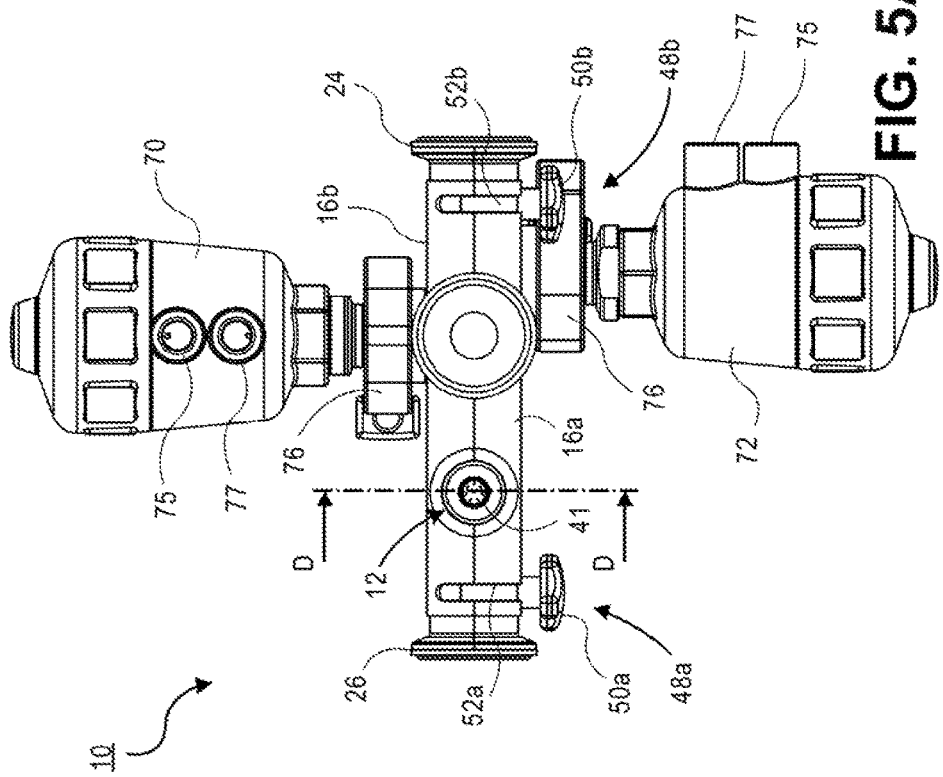
FIG. 5B illustrates a cross-sectional view of the fluid monitoring assembly taken along the line D-D of FIG. 5A.
Figure 5C:
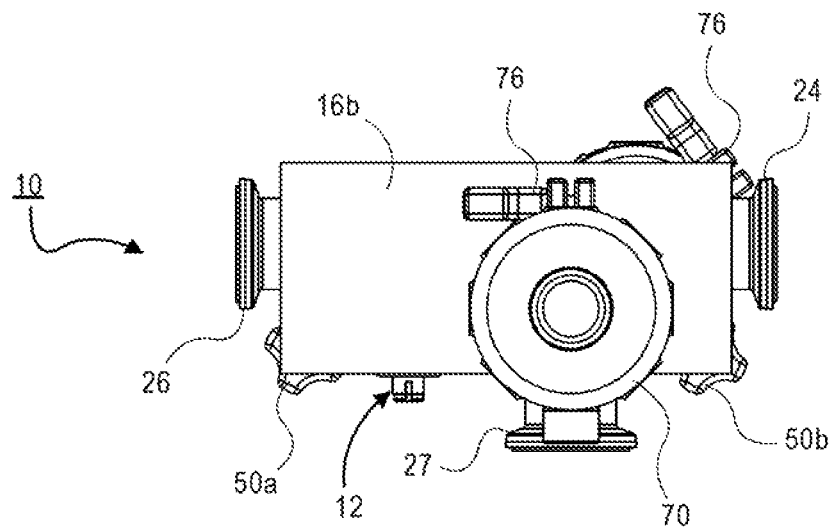
FIG. 5C illustrates end view of the fluid monitoring assembly of FIG. 5A.
Figure 5D:
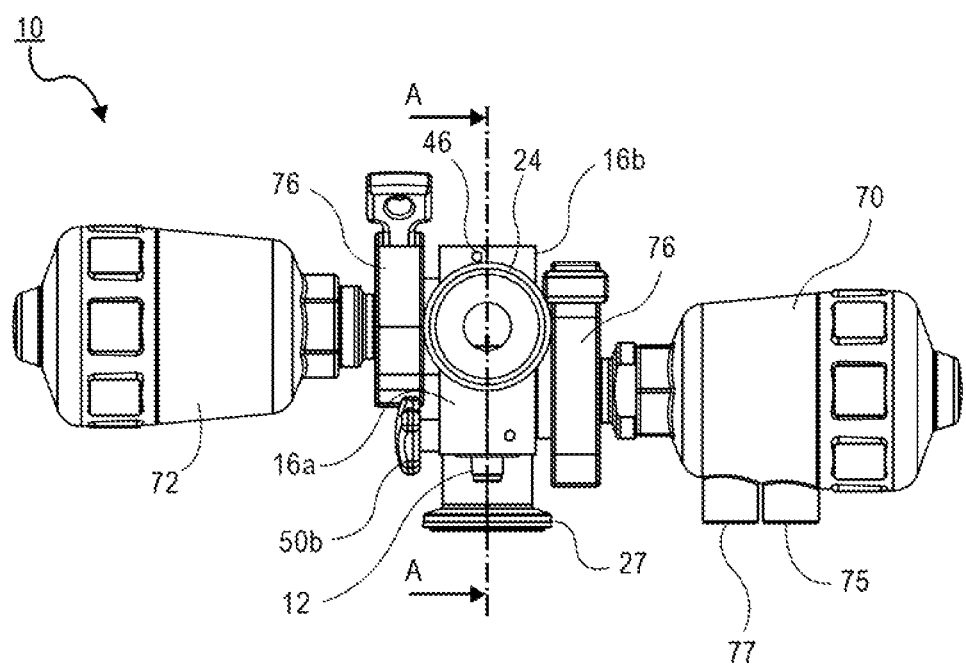
FIG. 5D illustrates top view of the fluid monitoring assembly of FIG. 5A.
Figure 5F:
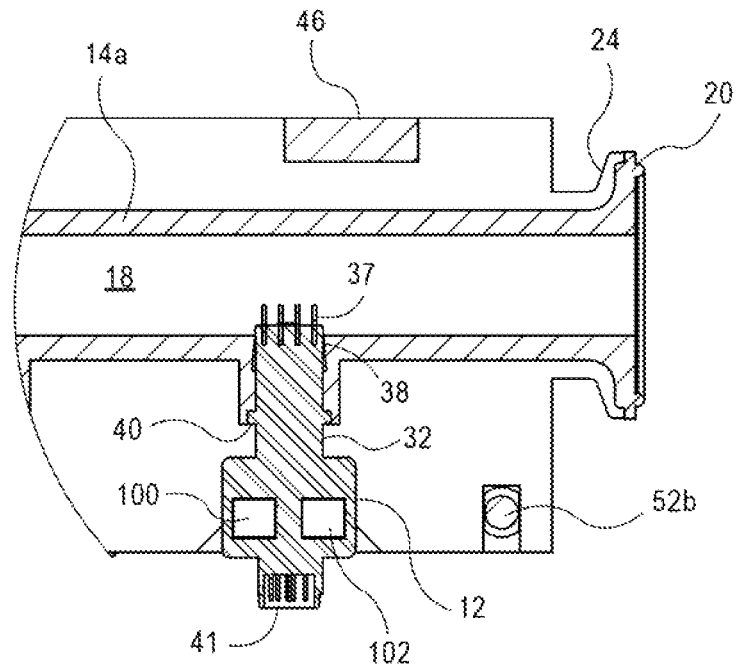
FIG. 5F illustrates a detailed view of detail E of FIG. 5E.
Figure 5E:
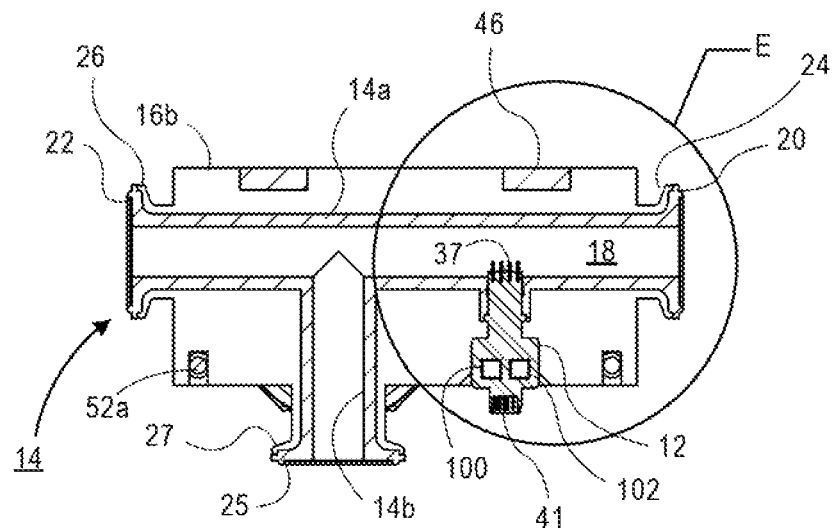
FIG. 5E illustrates a cross-sectional view of the fluid monitoring assembly taken along the line A-A of FIG. 5D.
Figure 6:
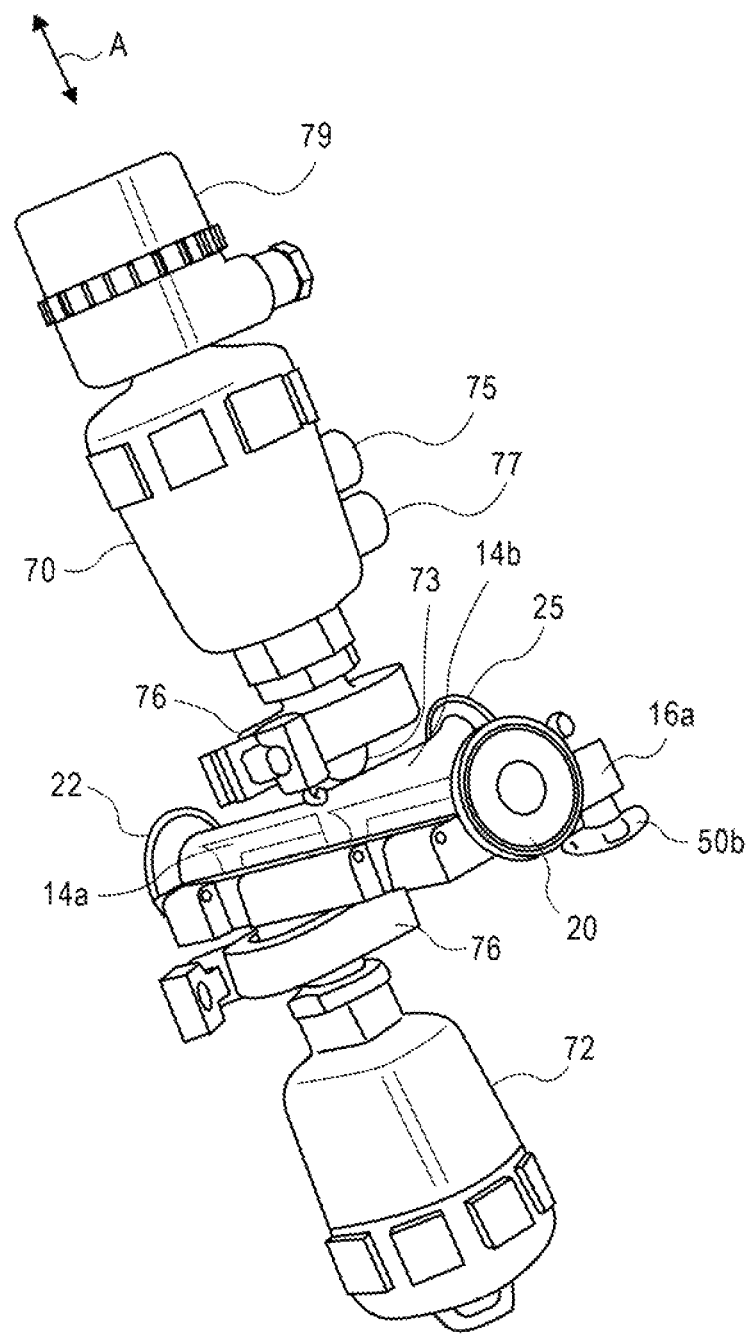
FIG. 6 illustrates a partial perspective view of the fluid monitoring assembly of FIG. 5A with one half of the housing removed to review certain inner components thereof.

FIGS. 5A-5F and 6 illustrate another embodiment of a fluid monitoring assembly 10. In this embodiment, similar elements to those described above are given similar reference numbers for sake of clarity. In this embodiment, unlike the prior embodiments, one or more valves 70, 72 are provided as part of the fluid monitoring assembly 10. The one or more valves 70, 72 are used to selectively close or open portions of the conduit 14. In the embodiment of FIGS. 5A-5F, and as illustrated in FIG. 5E, the conduit 14 includes a main conduit line 14a and a branch conduit line 14b. The ends of the main conduit line 14a terminate in flanges 20, 22 as in the prior embodiment although these are not mandatory. The branch conduit line 14b also terminates in a flange 25 which, again, is not mandatory depending on the fluid configuration. Flange 25 of the branch conduit line 14b is encapsulated (when housing 16 is closed via housing flange 27). In this embodiment, one valve 72 is mounted on one housing half 16a at a location such that actuation of the valve 72 moves an actuating element 73 as best seen in FIG. 6 to extend axially relative to the long axis (arrow A) of the valve 72 to pinch the underlying main conduit line 14a (FIG. 6 illustrates the actuating element 73 for valve 70 and the same exists for valve 72). By pinching the main conduit line 14a, fluid does not flow past this pinch point. Of course, the valve 72 may also be actuated to open fluid flow within the main conduit line 14a in which chase the actuating element 73 retracts in the opposite direction. In this regard, flow can be selectively modulated by actuation of the valve 72. The second valve 70 (seen in FIGS. 5A, 5B, 5C, 5D and 6) is mounted on the opposing housing half 16b (not illustrated in FIG. 6) at a location such that that its actuating element 73 extends axially to pinch the underlying branch conduit line 14b. In this manner, fluid may be selectively diverted, for example, into the main conduit line 14a. As one example, fluid may flow only in the main conduit line 14a. A sensor 12 as illustrated in FIGS. 5A-5E (or of any of the type described herein) may be used to monitor this fluid. For example, in this example, the sensor 12 is a conductivity sensor and measures the conductivity of the fluid passing therein. If the fluid conductivity that is measured by the sensor 12 is abnormal or out of the required range, fluid may be prevented from leaving the main conduit line 14a and and/or instead diverted to the branch conduit line 14b (e.g., a bypass line) by actuation of the valves 70, 72. In one example, valve 70 (for branch conduit 14b) may be closed while valve 72 (for main line conduit 14a) is open to prevent flow into the branch conduit line 14b. Upon detection of an abnormal conductivity, for example, when a measured parameter crosses a threshold value (e.g., goes above or below a threshold value), valve 70 may then open and valve 72 may close. This would then shunt fluid to the branch conduit 14b. Conversely, fluid may be diverted to the branch conduit 14b until the conductivity has reached an acceptable level whereby flow to the branch conduit 14b is stopped and fluid then passes through the main conduit line 14a. It should be understood that a wide variety of flow patterns and configurations may be made depending configuration of the conduit 14 and the number of valves 70, 72 which may vary.

The valves 70, 72 may be any number of types of valves commonly known to those skilled in the art. For example, the valves 70, 72 may be manual valves whereby a bonnet or the like is rotated manually to advance/retract the actuator 44. Alternatively, the valves 70, 72 may be automatically actuated valves such as pneumatically-actuated valves using air ports 75, 77 such as those illustrated in FIGS. 5A-5D, 6. These valves 70, 72 are actuated with the aid of gas lines connected thereto (not shown) that computer-controlled using an electro-pneumatic system incorporated into the valve design. The valves 70, 72 may also include an optional position feedback indicator 79 as illustrated in FIG. 6 that indicates the position or state of the valve 70, 72 (e.g., open or closed). The valves 70, 72 may also be electrically-actuated pinch valves. Such valves may be toggled between on/off states or in other instances may be partially opened or closed for fine modulating control. Other types of valves 70, 72 that may be used in connection with the fluid monitoring assembly 10 include diaphragm, solenoid, plug, globe, butterfly, gate valves and the like.

FIG. 5A illustrates a side view of fluid monitoring assembly 10 with the housing halves 16a, 16b in a closed state about the conduit 14 and the sensor. A pair of fasteners 48a, 48b with respective locking knobs 50a, 50b and associated hinged, locking arms 52a, 52b as explained herein can be used to fixedly hold the two-part housing 16 in the closed state. As seen in FIG. 5B, the housing halves 16a, 16b are connected via hinge 46. The respective valves 70, 72 may be mounted to the housing halves 16a, 16b using a clamp or collar 76. The clamp or collar 76 may surround matting flanges from adjacent components. Still referring to FIG. 5A, a sensor 12 in the form of a conductivity sensor (in this particular embodiment) extends through the housing halves 16a, 16b along a parting line and secured to a sensor mount 28 as described previously herein. FIGS. 5E and 5F illustrate the electrode pins of the sensing element 37 projecting into the lumen 18 of the main conduit line 14a.

FIG. 6 illustrates a partial perspective view of the fluid monitoring assembly of FIG. 5A with one half of the housing removed to review certain inner components thereof. Actuation of the valve 70 in this embodiment moves the actuating element 73 downward (in the direction of arrow A) to pinch and close off fluid flow within the branch line conduit 14b. In this embodiment, computer controlled pneumatic lines that interface with air ports 75, 77 are used to trigger movement of actuating element 73 in the downward or upward directions.

Figure 7:
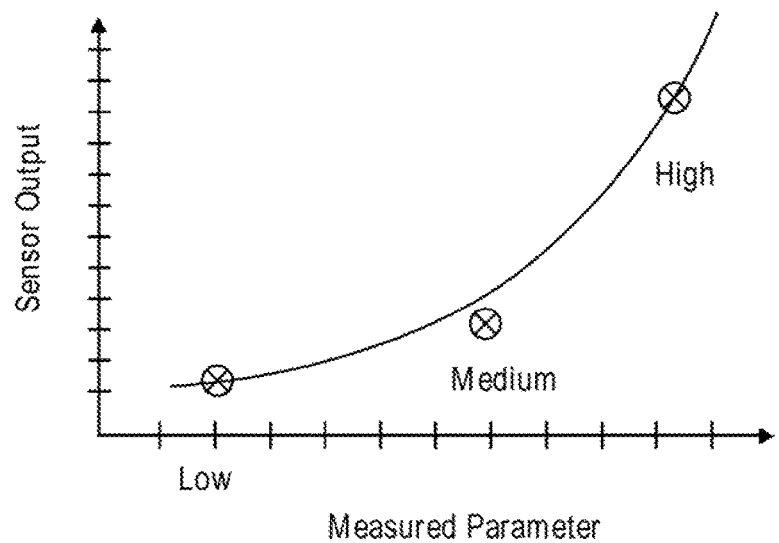
FIG. 7 is an illustration of multiple calibration points and a function or graph for those points as contemplated as one aspect of the invention.

FIG. 7 illustrates one example of exemplary calibration data that is stored in the memory 100 of the sensor 12. The calibration data may include, for example, a plurality (two or more) of calibration points. For example, different calibration points may be needed to measure the response of the sensor 12 over a variety of parameter conditions. Consider, for example, a conductivity sensor 12. Multiple calibration points may be provided spanning a range of conductivity values. For example, calibration points may be provided for a low conductivity value, a medium conductivity value, and a high conductivity value. Such as scheme is illustrated in FIG. 7. By storing multiple calibration points in the memory 100 more accurate sensor readings may be obtained over a larger measured parameter range. In addition, the memory 100 may also store a function or curve that fits the multiple calibration points. In this regard, a single function may be obtained from the memory 100 which can readily be used to translate measured readings from a sensor 12 to accurate results without the need to interpolate. The function or curve may be stored separately or in addition to the plurality of calibration points. The sensor 12 may be calibrated by exposing the sensor 12 to a fluid having a known parameter (e.g., temperature, pressure, pH, conductivity, concentration) and measuring the response of the sensor (e.g., voltage output). The response of the sensor 12 from the true or ideal response may be represented by an offset in the sensor output. As explained herein, multiple calibration points may be used for the sensor 12 at different parameter values (e.g., low, medium, high). Likewise, rather than a particular offset for one of these ranges, a function or curve may be generated that can be used to generate the output at any reading with the function or curve generated by curve fitting techniques or the like.

Figure 8:
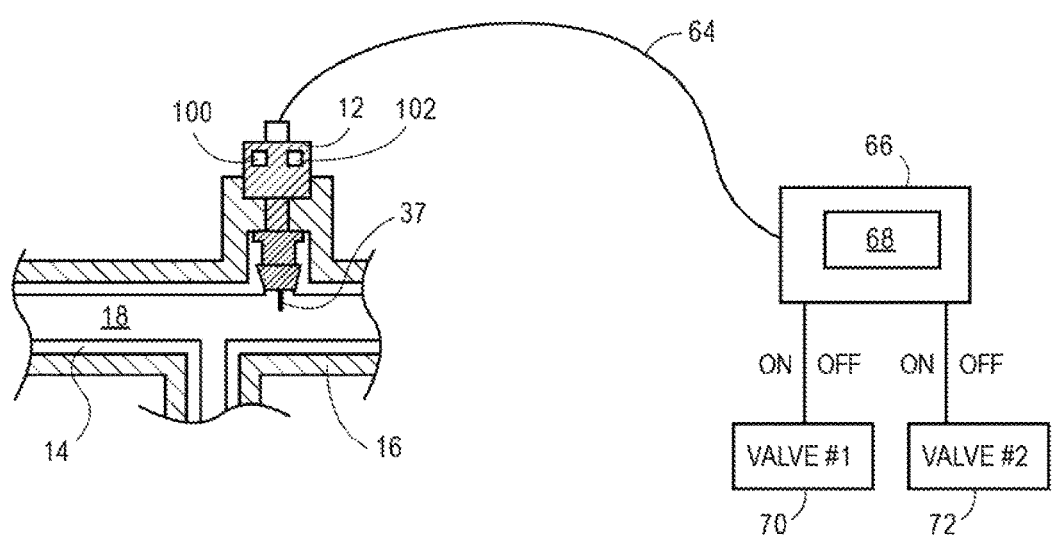
FIG. 8 is a schematic representation of a sensor coupled to a reading device/controller according to another embodiment.

FIG. 8 illustrates a single sensor 12 located in a conduit 14 and housing or jacket 16 that is connected via a cable 64 secured to connector 41 to a sensor reader device 66. The connector 41 may interface with sensor circuitry 102 that also is associated with or otherwise contains a memory 100. This could also be performed wirelessly instead of requiring a direct connection. The sensor reader device 66 may include circuitry therein that is operatively coupled to the sensing element 37 of the sensor 12 and receives data generated by the sensor 12 when fluid is in the presence of the sensing element 37. The sensor reader device 66 is also able to read the data stored in the memory 100 if such a memory is used in connection with the sensor 12. The sensor reader device 66 may include an optional display 68 or the like to display readings from the sensor 12. The sensor reader device 66 may also be incorporated into functionality of a controller device that can be used to control, for example, valves 70, 72. For instance, the controller device may be able to selectively turn on/off valves 70, 72 in response to measured readings at the sensor 12. Note that these valves 70, 72 may be located in the same unit housing the sensor 12, for example, as described in the context of the embodiment of FIGS. 5A-5E and 6. The sensor reader device 66 is able to compensate raw readings from the sensor 12 using calibration data stored in the optional memory 100. While FIG. 8 illustrates a sensor reader device 66 connected via a cable 64 sensor data may also be transferred wirelessly through a transmitter/receiver combination (not shown). In addition, the sensor reader device 66 may be able to receive data from multiple sensors 12.

While the male projection or barb 38 is illustrated in the drawings as having a triangular cross-section it should be understood that the male projection or barb 38 may take on any number of shapes or profiles which may include polygonal or curved aspects. In addition, in some alternative embodiments, the inner recess 54 of the mount 28 may be omitted entirely in which case the male projection or barb 38 may interface with a smooth walled inner surface of the mount 28. Further, as another alternative configuration, the male projection or barb 38 may be located on the inner surface of the mount 28 and the recess (akin to inner recess 54) may be positioned about the exterior of the elongate body portion 32. In this alternative configuration, the "female" recess is located on the sensor 12 while the male projection or barb 38 is located on the mount 28.

While the illustrated embodiments illustrate a single sensor 12 being located within a conduit 14 and housing 16 it should be understood that multiple sensors 12 may be located within a fluid monitoring assembly 10. For example, a UV sensor 12 may be combined with a conductivity sensor 12 as one example. Another example would include a temperature sensor 12 and a conductivity sensor 12. Further, multiple sensors 12 may be located within a housing 16 with or without valves 70, 72.

It should be understood that while many different embodiments are discussed herein, different embodiments may incorporate features or elements of other embodiments even though there are not specifically mentioned herein. For example, the feature and constructions of the sensor 12, conduit 14, and housing 16 may have features that are interchangeable and usable with other embodiments. While embodiments of the present invention have been shown and described, various modifications may be made without departing from the scope of the present invention. The invention, therefore, should not be limited, except to the following claims and their equivalents.

What is claimed is:

1. A fluid monitoring assembly comprising:
a segment of replaceable, flexible conduit comprising a wall defining a lumen through which the fluid passes;
a sensor mount integrally formed with the wall of the segment of replaceable, flexible conduit and extending generally transverse with respect to a longitudinal axis of the segment of replaceable, flexible conduit, the sensor mount including an aperture having a seat formed therein and defining a female shaped inner surface extending through the sensor mount to the lumen of the segment of replaceable, flexible conduit;
a sensor configured to be removably secured within the sensor mount, the sensor having an elongate body terminating at one end thereof in a sensing portion, the elongate body having a male projection on a portion thereof and configured to rest within the female shaped inner surface when secured within the sensor mount, the elongate body further comprising a flange that rests on the seat and wherein the sensing portion is exposed to the lumen of the segment of replaceable, flexible conduit; and
a housing having first and second portions connected to one another at a hinge, the housing defining an interior portion configured to encapsulate the segment of replaceable, flexible conduit, the elongate body of the sensor including the flange, and the sensor mount.

2. The fluid monitoring assembly of claim 1, the housing further comprising at least one fastener configured to secure the first and second portions of the housing in a closed state.

3. The fluid monitoring assembly of claim 1, wherein the housing comprises metal or polymer.

4. The fluid monitoring assembly of claim 1, wherein the sensor comprises one of a pressure sensor, a conductivity sensor, a temperature sensor, and a pH sensor.

5. The fluid monitoring assembly of claim 1, wherein the male projection comprises a barbed end.

6. The fluid monitoring assembly of claim 1, wherein the segment of replaceable, flexible conduit comprises at least one of silicone, thermoplastic elastomer, or thermoplastic rubber.

7. The fluid monitoring assembly of claim 1, wherein the sensor comprises a memory configured to store calibration data therein.

8. A fluid monitoring assembly comprising:
- a segment of replaceable, flexible conduit comprising a wall defining a lumen through which the fluid passes;
- a sensor mount integrally formed with the wall of the segment of replaceable, flexible conduit and extending generally transverse with respect to a longitudinal axis of the segment of replaceable, flexible conduit, the sensor mount including an aperture having a seat formed therein and extending through the sensor mount and into the lumen of the segment of replaceable, flexible conduit, the aperture defining a female shaped inner recess;
- a sensor configured to be removably secured within the sensor mount, the sensor having an elongate body terminating at one end thereof in a sensing portion, the elongate body having a male projection on a portion thereof and configured to rest within the female shaped inner recess when secured within the sensor mount, the elongate body further comprising a flange that rests on the seat and wherein the sensing portion is exposed to the lumen of the segment of replaceable, flexible conduit;
- a housing having first and second portions, wherein an interior portion of the first and second portions are configured to encapsulate the segment of replaceable, flexible conduit, the elongate body of the sensor including the flange, and the sensor mount; and
- one or more pinch valves disposed on the housing and configured to pinch the segment of replaceable, flexible conduit.

9. The fluid monitoring assembly of claim 8, wherein the sensor comprises one of a conductivity sensor, a pressure sensor, a temperature sensor, or a pH sensor.

10. The fluid monitoring assembly of claim 8, wherein the male projection comprises a barbed end.

11. The fluid monitoring assembly of claim 8, wherein the segment of replaceable, flexible conduit comprises at least one of silicone, thermoplastic elastomer, or thermoplastic rubber.

12. The fluid monitoring assembly of claim 8, wherein the sensor comprises a memory configured to store a plurality of calibration points or a calibration curve or function.

13. A method of changing a fluid monitoring assembly comprising a segment of replaceable, flexible conduit comprising a wall defining a lumen through which the fluid passes, a sensor mount integrally formed with the wall of the segment of replaceable, flexible conduit and extending generally transverse with respect to a longitudinal axis of the segment of replaceable, flexible conduit, the sensor mount including an aperture having a seat formed therein and defining female shaped inner surface extending through the sensor mount to the lumen, a sensor configured to be removably secured within the sensor mount, the sensor having an elongate body terminating at one end thereof in a sensing portion, the elongate body having a male projection on a portion thereof and configured to rest within the female shaped inner surface when secured within the sensor mount, the elongate body further comprising a flange that rests on the seat and wherein the sensing portion is exposed to the lumen of the segment of replaceable, flexible conduit, the fluid monitoring assembly further comprising a housing configured to encapsulate the segment of replaceable, flexible conduit, the elongate body of the sensor including the flange, and the sensor mount, the method comprising:
- opening the housing;
- removing at least one of the sensor and the segment of replaceable, flexible conduit;
- inserting a replacement for the removed sensor and/or segment of replaceable, flexible conduit; and
- closing the housing.

14. The method of claim 13, wherein opening the housing comprises opening first and second halves of the housing.

15. The method of claim 14, wherein the first and second halves are connected via a hinge.

16. The method of claim 14, further comprising securing the first and second halves together via one or more fasteners.

17. The method of claim 13, wherein the housing comprises at least one pinch valve mounted thereon.

18. The method of claim 13, wherein the segment of replaceable, flexible conduit is replaced and utilizes the same sensor.

19. The method of claim 13, wherein the segment of replaceable, flexible conduit and the sensor are replaced.

* * * * *